United States Patent
Hossainy et al.

(10) Patent No.: US 9,456,983 B1
(45) Date of Patent: Oct. 4, 2016

(54) THERAPEUTIC COMPOSITION WITH ENHANCED VESSEL TARGETING

(75) Inventors: Syed Faiyaz Ahmed Hossainy, Fremont, CA (US); Florian Niklas Ludwig, Mountain View, CA (US); Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 2541 days.

(21) Appl. No.: 11/636,092

(22) Filed: Dec. 8, 2006

(51) Int. Cl.
*A61K 9/14* (2006.01)
*A61K 9/10* (2006.01)
*A61K 9/16* (2006.01)

(52) U.S. Cl.
CPC ............... *A61K 9/10* (2013.01); *A61K 9/1641* (2013.01)

(58) Field of Classification Search
CPC .......... A61K 9/10; A61K 9/14; A61K 9/141; A61K 9/143; A61K 9/145; A61K 9/16; A61K 9/1641; A61K 9/1682; A61K 9/167
USPC ................. 424/422, 450–452, 456, 457, 460
See application file for complete search history.

(56) References Cited

U.S. PATENT DOCUMENTS

| | | | |
|---|---|---|---|
| 5,686,103 A * | 11/1997 | Redziniak et al. | 424/450 |
| 6,168,804 B1 | 1/2001 | Samuel et al. | |
| 6,258,378 B1 | 7/2001 | Schneider et al. | |
| 6,268,222 B1 * | 7/2001 | Chandler et al. | 436/523 |
| 6,451,338 B1 | 9/2002 | Gregoriadis et al. | |
| 2002/0151004 A1 * | 10/2002 | Craig | 435/173.1 |
| 2002/0187184 A1 * | 12/2002 | Golomb et al. | 424/450 |
| 2003/0137067 A1 * | 7/2003 | Cooper et al. | 264/5 |
| 2004/0023855 A1 * | 2/2004 | John et al. | 514/8 |
| 2004/0109823 A1 * | 6/2004 | Kaplan | 424/1.11 |
| 2004/0143064 A1 * | 7/2004 | Wang | 525/191 |
| 2007/0190160 A1 * | 8/2007 | Turos et al. | 424/490 |

OTHER PUBLICATIONS

Kim et al (Polymeric worm micelles as nano-carriers for drug delivery; Nanotechnology; 16 (2005) S484-S491).*
H. Goldsmith, "Hemostasis and thrombosis" vol. 1, Edited by T. Spaet pp. 97-139, 1972.

* cited by examiner

*Primary Examiner* — Micah-Paul Young
(74) *Attorney, Agent, or Firm* — Squire Patton Boggs (US) LLP

(57) ABSTRACT

A composition that includes a bioactive agent-containing polymeric nanoparticle and a polymeric non-spherical microparticle, and methods of using such a composition to treat a vascular disease are disclosed.

41 Claims, No Drawings

THERAPEUTIC COMPOSITION WITH ENHANCED VESSEL TARGETING

FIELD OF THE INVENTION

The present invention relates to a composition that includes polymeric nanoparticles and polymeric non-spherical microparticles, and methods of using the composition for treating a vascular disease.

BACKGROUND OF THE INVENTION

The traditional method of administering therapeutic agents to treat diseases of the internal organs and vasculature has been by systemic delivery. Systemic delivery involves administering a therapeutic agent at a discrete location followed by the agent migrating throughout the patient's body including, of course, to the afflicted organ or area of the vasculature. But to achieve a therapeutic amount of the agent at the afflicted site, an initial dose substantially greater than the therapeutic amount must be administered to account for the dilution the agent undergoes as it travels through the body. Systemic delivery introduces the therapeutic agent in two ways: into the digestive tract (enteral administration) or into the vascular system (parenteral administration), either directly, such as injection into a vein or an artery, or indirectly, such as injection into a muscle or into the bone marrow. Absorption, distribution, metabolism, excretion and toxicity, the ADMET factors, strongly influence delivery by each of these routes. For enteric administration, factors such as a compound's solubility, its stability in the acidic environs of the stomach and its ability to permeate the intestinal wall all affect drug absorption and therefore its bioavailability. For parenteral delivery, factors such as enzymatic degradation, lipophilic/hydrophilic partitioning coefficient, lifetime in circulation, protein binding, etc. will affect the agent's bioavailability.

At the other end of the spectrum is local delivery, which comprises administering the therapeutic agent directly to the afflicted site. With localized delivery, the ADMET factors tend to be less important than with systemic administration because administration is essentially directly to the treatment site. Thus, the initial dose can be at or very close to the therapeutic amount. With time, some of the locally delivered therapeutic agent may diffuse over a wider region, but that is not the intent of localized delivery, and the diffused agent's concentration will ordinarily be sub-therapeutic, i.e., too low to have a therapeutic effect. Since localized delivery targets only the afflicted region, reoccurrence of the disease is possible because causal factors of the disease that may have spread to as yet non-afflicted regions at the periphery of the afflicted region may not undergo sufficient treatment.

There is, therefore, a need for drug delivery systems that can be applied locally to treat regional disorders.

The present invention provides a microparticle and nanoparticle composition as well as a method of using these compositions, to accomplish this objective.

SUMMARY OF THE INVENTION

The present invention relates to a composition that includes a plurality of polymeric nanoparticles that include a first bioactive agent encapsulated within, adhered to a surface of or integrated into the structure of the nanoparticles, and a plurality of polymeric non-spherical microparticles having a high surface-area-to-volume ratio and optionally including a second bioactive agent, which may be the same as, or different from, the first bioactive agent, encapsulated within, adhered to a surface of or integrated into the structure of the microparticle.

In various aspects, the smallest linear dimension of the microparticle is at least 4 times larger, at least 3 times larger or at least 2 times larger than the largest linear dimension of the nanoparticle. The microparticle has a minimum linear dimension of 1 micron. The nanoparticle has a maximum linear dimension of 500 nanometers.

The nanoparticle can be a micelle, a liposome, a polymersome, a hydrogel particle or a polymer particle. The microparticle can be a polymer particle, a polymersome or a hydrogel particle.

In various aspects, the microparticle can be irregular-, oblong-, spindle-, rod-, cylindrical-, pancake-, discoid-, or red blood cell-shaped. The microparticle can be a hydrogel particle. In some hydrogel embodiments, the microparticle comprises a polymer selected from a group that includes hyaluronic acid, poly(vinyl pyrrolidone), poly(ethylene glycol), albumin, poly(vinyl alcohol), gelatin, chitosan, alginate, fibrin and collagen.

In one embodiment, the nanoparticles and microparticles are made of the same polymer or polymers. In other embodiments, the microparticles include carbon nanotubes, where the carbon nanotubes can be single or multi-walled. In further embodiments, the microparticles can be flexible or rigid polymeric cylinders, worm micelles, flexible polymeric or lipid membranes or flaccid polymersomes or liposomes.

In an aspect of the present invention, the microparticle has a surface-area-to-volume aspect ratio between 0.1 and 100, more preferably between 1 and 10.

In an aspect of the present invention, the microparticles can include a biodegradable or bioerodable material. In various embodiments, the microparticles biodegrade or bioerode within 1.0 second to 100 hours, preferably at present within 10.0 seconds to 10 hours or most preferably at present within 1.0 minute to 1 hour.

In an aspect of the present invention, the nanoparticles can include a biodegradable or bioerodable material. In various embodiments, the nanoparticles biodegrade or bioerode within 1.0 second to 100 hours, preferably at present within 10.0 seconds to 10 hours or most preferably at present within 1.0 minute to 1 hour.

In one embodiment, the nanoparticles comprise a functional group operatively coupled to their surface. In this embodiment, the functional group has binding affinity for endothelium. The functional group can be a peptide, a protein such as without limitation an antibody, or an oligonucleotide such as without limitation an aptamer. The functional group can have a charge.

In various other aspects, the first and second bioactive agents can be, without limitation, a corticosteroid, everolimus, zotarolimus, sirolimus, sirolimus derivatives, paclitaxel, a bisphosphonate, ApoA1, a mutated ApoA1, ApoA1 milano, an ApoA1 mimetic peptide, an anti-inflammatory agent, an anti-proliferative agent, an anti-angiogenic agent, a matrix metalloproteinase inhibitor and a tissue inhibitor of metalloproteinase.

Another aspect of the present invention relates to a method for treating a vascular disease that includes providing a composition of the present invention and administering the composition to a vascular disease locale in a patient.

In one embodiment, administering the composition to a vascular disease locale in a patient includes intraarterial delivery, including percutaneous transluminal coronary arterial delivery and coaxial delivery of the nanoparticles and microparticles.

In a further embodiment, intraarterial delivery includes using a catheter, including using a guiding, diagnostic or drug-delivery catheter.

DETAILED DESCRIPTION OF THE INVENTION

In many instances, localized intravascular administration of therapeutic agents would comprise a significant improvement in the art. But there are special considerations that must be taken into account in the development of a localized, intravascular drug-delivery system. For example, the system should minimize clotting or thrombogenesis.

Moreover, constant blood flow through the vasculature results in rapid dilution of the drug. There is, therefore, a need for a drug delivery system that can safely be delivered intravascularly and which can remain at the site to release therapeutic agent for a time.

The present invention provides a system of injectable microparticles and nanoparticles to safely locally administer therapeutic agents that will remain at the site for an extended time. Nanoparticles can enter cells and penetrate intracellular junctions. But an ability to confer cell adhesion properties to nanoparticles to enhance adhesion of the nanoparticles at the site, i.e., the extracellular matrix in a vessel wall or the surrounding tissue, thereby facilitating local drug retention, is lacking in the art.

Thus, biodegradable sustained release nanoparticles that could preferentially locate at a vessel wall would be extremely valuable in treating cardiovascular diseases, such as restenosis, atherosclerosis, vulnerable plaque and peripheral arterial disease.

The present invention relates to a composition that includes a plurality of polymeric nanoparticles that include a first bioactive agent encapsulated within, adhered to a surface of or integrated into the structure of the nanoparticles, and a plurality of polymeric non-spherical microparticles having a high surface-area-to-volume ratio and optionally including a second bioactive agent that may be the same as, or different from, the first bioactive agent, encapsulated within, adhered to a surface of or integrated into the structure of the microparticle.

As used herein, "polymeric nanoparticle" refers to a microscopic particle, composed of one or more polymers, whose size in nanometers (nm) includes a maximum linear dimension of less than 500 nanometers. As used herein, linear dimension refers to the distance between any two points on a nanoparticle as measured in a straight line. Nanoparticles of the present invention can be irregular-, oblong-, spindle-, rod-, cylindrical-, pancake-, discoid-, or red blood cell-shaped but are preferably spherical or substantially spherical.

As used herein, substantially spherical refers to a shape that is not perfectly spherical but has a generally spherical shape, e.g., an ellipsoid.

As used herein, a "polymer" refers to a molecule(s) composed of a plurality of repeating structural units connected by covalent chemical bonds.

Several types and configurations of nanoparticles are encompassed by the present invention. For example, nanoparticles may be composed of a range of materials including, but not limited to, a biostable polymer, a biodurable polymer, a bioabsorbable polymer or a combination thereof. Biostable refers to polymers that are not degraded in vivo, i.e., are not biodegradable. The terms biodegradable, bioabsorbable, and bioerodable, as well as degraded, eroded, and absorbed, are used interchangeably (unless the context shows otherwise) and refer to polymers that are capable of being degraded or absorbed after being delivered to a disease locale in a patient, e.g., when exposed to bodily fluids such as blood, and that can be gradually resorbed, absorbed, and/or eliminated by the body.

Suitable nanoparticles include micelles, liposomes, polymersomes, hydrogel particles and polymer particles.

As used herein, a "micelle" refers to an aggregate, e.g., a cluster, of surfactant molecules. Micelles are formed when the concentration of surfactant is above the critical micelle concentration. "Surfactants" refer to chemicals that are amphipathic, i.e., they contain both hydrophobic and hydrophilic groups. Micelles can exist in different shapes, including spherical, cylindrical, and discoidal. Micelles may be stabilized by crosslinking the surfactant molecules that form the micelle.

As used herein, a "liposome" refers to a compartment that is completely enclosed by a bilayer typically composed of phospholipids. Liposomes are prepared according to standard techniques known to those skilled in the art. For example, without limitation, suspending a suitable lipid, e.g., phosphatidyl choline, in an aqueous medium followed by sonication of the mixture will form a liposome. Alternatively, rapidly mixing a solution of lipid in ethanol-water, for example, by injecting a lipid through a needle into an agitated ethanol-water solution can form lipid vessicles. Liposomes can also be composed of other amphiphilic substances, e.g., shingomyelin or lipids containing poly (ethylene glycol) (PEG).

As used herein, a "polymersome" refers to diblock copolymers that are modified to form bilayer structures similar to liposomes. Depending on the length and composition of the polymers in the diblock copolymer, polymersomes can be substantially more robust that liposomes. In addition, the ability to control the chemistry of each block of the diblock copolymer permits tuning of the polymersome's composition to fit the desired application. For example, membrane thickness can be controlled by varying the degree of polymerization of the individual blocks. Adjusting the glass transition temperatures of the blocks will affect the fluidity and therefore the permeability of the membrane. Even the mechanism of release can be modified by altering the nature of the polymers.

Polymersomes can be prepared in essentially the same manner as liposomes. That is, dissolving the copolymer in an organic solvent, applying the solution to a vessel surface, and then removing the solvent, leaves a film of diblock copolymer on the vessel wall. The film is then hydrated to form polymersomes. Dissolving the diblock copolymer in a solvent and then adding a weak solvent for one of the blocks, will also create polymersomes.

As with liposomes, polymersomes can be used to encapsulate bioactive agents by including the bioactive agent in the water used to rehydrate the copolymer film. Osmotically driving the bioactive agent into the core of the polymersomes is known as force loading. Using a double emulsion technique, polymersomes of relative monodispersivity and high loading efficiency are possible. The technique involves using microfluidic technology to generate double emulsions comprising water droplets surrounded by a layer of organic solvent. These droplet-in-a-drop structures are then dispersed in a continuous water phase. The diblock copolymer is dissolved in the organic solvent and self-assembles into proto-polymersomes on the concentric interfaces of the double emulsion. Completely evaporating the organic solvent from the shell yields the actual polymersomes. This procedure allows fine control over the polymersome size. In addition, the ability to maintain complete separation of the internal fluids from the external fluid throughout the process allows extremely efficient encapsulation.

As used herein, a hydrogel particle refers to a loosely cross-linked network of polymer chains that is superabsorbent but stable in an aqueous environment. Hydrogel particles can be used to encapsulate bioactive agents by methods known to those skilled in the art.

As used herein, a polymer particle refers to a solid particle, in contrast to the shell structure of liposomes and polymersomes and the relatively open structures of hydrogel particles.

Polymers that may be used to prepare nanoparticles and microparticles of this invention include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrin glue, fibrinogen, cellulose, starch, collagen and hyaluronic acid, elastin and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates including tyrosine-based polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, carboxymethyl cellulose, fullerenes and lipids.

A nanoparticle of this invention has a first bioactive agent encapsulated within, adhered to the surface of, or integrated into its structure.

As used herein, "encapsulated within" means the first bioactive agent is substantially enclosed within the nanoparticle.

As used herein, "adhered to the surface of" means the first bioactive agent is covalently or non-covalently attached to the outer surface of the nanoparticle.

As used herein, "integrated into the structure of" means the bioactive agent is part of the chemical structure of the material forming the nanoparticle.

As used herein, a "bioactive agent" refers to any substance that is of medical or veterinary therapeutic or prophylactic utility.

A therapeutic bioactive agent further refers to a bioactive agent that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to regress; or (4) alleviating one or more symptoms of the disease.

A bioactive agent also refers to an agent that, when administered to a patient, either prevents the occurrence of a disease or disorder or retards the recurrence of the disease or disorder. Such a bioactive agent may be referred to as a prophylactic bioactive agent.

Suitable bioactive agents include, without limitation, anti-proliferative agents, anti-inflammatory agents, antineoplastics and/or antimitotics, antiplatelet, anticoagulant, antifibrin, and antithrombin drugs, cytostatic or antiproliferative agents, antibiotics, antiallergic agents, antioxidants and other bioactive agents known to those skilled in the art.

Suitable antiproliferative agents include, without limitation, actinomycin D, or derivatives or analogs thereof, i.e., actinomycin D is also known as dactinomycin, actinomycin IV, actinomycin $I_1$, actinomycin $X_1$, and actinomycin $C_1$. Antiproliferative agents can be natural proteineous agents such as a cytotoxin or a synthetic molecule, all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin, prodrugs thereof, co-drugs thereof, and combinations thereof.

Suitable anti-inflammatory agents include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of proinflammatory signaling molecules including antibodies to such biological inflammatory signaling molecules.

Suitable antineoplastics and/or antimitotics include, without limitation, paclitaxel, docetaxel, methotrexate, azathioprine, vincristine, vinblastine, fluorouracil, doxorubicin hydrochloride, and mitomycin.

Suitable antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä (Biogen, Inc., Cambridge, Mass.), calcium channel blockers (such as nifedipine), colchicine, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other bioactive substances or agents that may be appropriate include alpha-interferon, and genetically engineered epithelial cells.

Suitable cytostatic or antiproliferative agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide.

Suitable antiallergic agents include, without limitation, permirolast potassium.

Other suitable bioactive agents include, without limitation, alpha-interferon, genetically engineered epithelial cells, dexamethasone and its derivatives, rapamycin derivatives and analogs such as 40-O-(2-hydroxyethyl)rapamycin (EVEROLIMUS®), 40-O-(3-hydroxypropyl)rapamycin, 40-O-[2-(2-hydroxyethoxy)]ethyl-rapamycin, and 40-O-tetrazolylrapamycin, synthetic inorganic and organic compounds, proteins and peptides, polysaccharides and other sugars, lipids, and DNA and RNA nucleic acid sequences having therapeutic, prophylactic or diagnostic activities, nucleic acid sequences include genes, antisense molecules which bind to complementary DNA to inhibit transcription, and ribozymes. Some other examples of suitable bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy; antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Presently preferred first and second bioactive agents are independently selected from the group including corticosteroids, everolimus, zotarolimus, sirolimus, paclitaxel, bisphosphonates, ApoA1, mutated ApoA1, ApoA1 milano, ApoA1 mimetic peptides, anti-inflammatory agents, antiproliferative agents, matrix metalloproteinase inhibitors and tissue inhibitors of metalloproteinases.

The amount of bioactive agent in a nanoparticle or microparticle will depend on the required minimum effective concentration (MEC) of the agent and the length of time over which it is desired that the MEC be maintained. For most bioactive agents the MEC will be known to, or readily derivable by, those skilled in the art from the literature. For experimental bioactive agents or those for which the MEC by localized delivery is not known, it can be empirically determined using techniques well-known to those skilled in the art.

A composition of the present invention includes a plurality of polymeric nanoparticles and a plurality of polymeric non-spherical microparticles, wherein the microparticles have a high surface-area-to-volume ratio and optionally comprise a second bioactive agent that may be the same as, or different from, the first bioactive agent, encapsulated within, adhered to a surface of or integrated into the structure of the microparticle.

As used herein, a polymeric non-spherical microparticle refers to a particle the smallest linear dimension of which is no less than about 1.0 micron.

Because nanoparticles of the present invention have a maximum linear dimension of no more than 500 nanometers and microparticles of the present invention have a minimum linear dimension of no less than 1.0 micron, the composition of the present invention consists of two distinct populations of particles. It is to be understood, however, that within the respective microparticle and nanoparticle populations, both unimodal and multi-modal sub-populations of particles are possible.

In some embodiments, the non-spherical microparticles include polymer particles, polymersomes and hydrogel particles.

Microparticles made of polymer particles, polymersomes and hydrogel particles can be made of the same materials as the nanoparticles described above.

As used herein, "non-spherical" refers to the physical shape of a microparticle of the invention. In some embodiments, the microparticles are irregular-, oblong-, spindle-, rod-, cylindrical-, pancake-, discoid-, or red blood cell-shaped.

The microparticles of the present invention comprise a high surface-area-to-volume aspect ratio, preferably between 0.1 and 100, more preferably between 1 and 10.

The microparticles optionally comprise a second bioactive agent that may be the same as, or different from, the first bioactive agent and may be encapsulated within, adhered to a surface of or integrated into the structure of the microparticle. Suitable bioactive agents are described above. Suitable methods of encapsulation, adherence and integration of the agent into the structure of microparticles are described above in relation to nanoparticles.

In certain embodiments, the microparticles comprise a hydrogel particle. Presently preferred hydrogel particles include polymers such as, without limitation, hyaluronic acid, polyvinyl pyrrolidone, poly(ethylene glycol), albumin, poly(vinyl alcohol), gelatin, chitosan, alginate, fibrin and collagen.

According to one embodiment of the present invention, the nanoparticle and microparticle comprise the same polymer or polymers.

In certain embodiments of this invention, the microparticle can be single or multi-walled carbon nanotubes, rigid or flexible polymeric cylinders, worm micelles, flexible polymeric or lipid membranes or flaccid polymersomes or flaccid liposomes.

As an embodiment of the invention, the microparticle can be made of a biodegradable or bioerodable material. Suitable biodegradable materials include naturally-occurring polymers such as, without limitation, collagen, chitosan, alginate, fibrin, fibrinogen, cellulosics, starches, dextran, dextrin, hyaluronic acid, heparin, glycosaminoglycans, polysaccharides and elastin.

One or more synthetic or semi-synthetic biodegradable polymers may also be used to make microparticles useful with this invention. As used herein, a synthetic polymer refers to one that is created wholly in the laboratory while a semi-synthetic polymer refers to a naturally-occurring polymer that has been chemically modified in the laboratory. Examples of synthetic polymers include, without limitation, polyphosphazines, polyphosphoesters, polyphosphoesterurethane, polyhydroxyacids, polyhydroxyalkanoates, polyanhydrides, polyesters, polyorthoesters, polyamino acids, polyoxymethylenes, poly(ester-amides) and polyimides.

In one embodiment of the present invention, the nanoparticle can include a functional group operatively coupled to its surface.

As used herein, "operatively coupled" refers to the attachment of a functional group to the surface of a nanoparticle through either direct or indirect means. For example, it is possible for a functional group to be directly attached to the surface of the nanoparticle by a portion of the functional group itself. Alternatively, it is possible that the functional group is attached to the surface of the nanoparticle via an intermediate component that couples the functional group with the surface of the nanoparticle. Such intermediate components are often referred to as linkers. Linkers are di-functional molecules that can have one moiety that chemically attaches to a nanoparticle and a second moiety that chemically attaches to a functional group. Any number of intermediate components are encompassed by the present invention, and are known to those skilled in the art.

When the nanoparticle has a functional group operatively coupled to its surface, the functional group can have binding affinity for endothelium and can be a peptide, a protein, e.g., an antibody or an antibody fragment, or an oligonucleotide, e.g., an aptamer. The functional group can also have a charge. Exemplary functional groups with binding affinity for endothelium include, without limitation, RGD peptides, antibodies, CD31 antibodies, antibody fragments or aptamers with affinity to E-selectin, vascular cell adhesion molecule-1 or intracellular adhesion molecule-1. Functional groups can be localized to the surface of the nanoparticle by anchoring them to the surface. For example, a functional group with affinity for endothelium can be covalently conjugated to the hydrophilic end of an amphiphilic molecule, such as a phospholipid with a hydrophilic spacer coupled to its headgroup, or an amphiphilic block co-polymer, such as PEG-PLA. These anchor conjugated functional groups may then be localized to the surface of a nanoparticle by co-incubation of the conjugate with pre-made nanoparticles, or by including a small amount of these conjugates during the formulation process, methods of which are known to those skilled in the art.

Another aspect of the present invention relates to a method for treating a vascular disease that includes providing a composition of the present invention and administering the composition to a vascular disease locale in a patient.

Administering the composition to a vascular disease locale in a patient includes intraarterial delivery of the composition. In certain embodiments, administering the composition to a vascular disease locale in a patient includes percutaneous transluminal coronary arterial delivery. In other embodiments, administering the composition to a vascular disease locale in a patient includes coaxial delivery of the nanoparticle and microparticle.

As used herein, "coaxial delivery" refers to the delivery of nanoparticles and microparticles along the same axis using, for example, without limitation, an apparatus that is composed of a first tubular body positioned within a second larger tubular body. For example, without limitation, the microparticles can be delivered by the first tubular body while the nanoparticles can be delivered by the second larger tubular body such that the nanoparticles move along the outside edge of the first tubular body yet inside of the second tubular body. Also encompassed is the delivery of nanoparticles via the first tubular body and delivery of the microparticles via the second larger tubular body. In both aspects, the nano- and micro-particles are delivered along the same axis.

In certain aspects, the second tubular body may have openings through which either microparticles or nanoparticles may move. In other aspects, the solution in which the nanoparticles and microparticles are dissolved will be viscous, with relation to the natural environment of the vasculature. Such solutions are known to those skilled in the art.

In certain embodiments, administering the composition to a vascular disease locale in a patient includes using a catheter, including guiding, diagnostic and drug delivery catheters.

As used herein, a "patient" refers to any organism that can benefit from the administration of a bioactive agent. In particular at present, patient refers to a mammal such as a cat, dog, horse, cow, pig, sheep, rabbit, goat or a human being.

As used herein, "treating" refers to the administration of a therapeutically effective amount of a bioactive agent to a patient known or suspected to be suffering from a vascular disease. Bioactive agents useful with this invention are described above. Bioactive agents include a corticosteroid, everolimus, zotarolimus, sirolimus, sirolimus derivatives, paclitaxel, a bisphosphonate, ApoA1, a mutated ApoA1, ApoA1 milano, an ApoA1 mimetic peptide, an anti-inflammatory agent, an anti-proliferative agent, an anti-angiogenic agent, a matrix metalloproteinase inhibitor and a tissue inhibitor of metalloproteinase.

As used herein, a "therapeutically effective amount" refers to the amount of bioactive agent that has a beneficial effect, which may be curative or palliative, on the health and well-being of a patient with regard to a vascular disease with which the patient is known or suspected to be afflicted. A therapeutically effective amount may be administered as a single bolus, as intermittent bolus charges, as short, medium or long term sustained release formulations or as any combination of these.

As used herein, "known" to be afflicted with a vascular disease refers first to a condition that is relatively readily observable and or diagnosable. An example, without limitation, of such a disease is atherosclerosis, which is a discrete narrowing of a patient's arteries. Restenosis, on the other hand, while in its latter stages, like atherosclerosis, is relatively readily diagnosable or directly observable, may not be so in its nascent stage. Thus, a patient may be "suspected" of being afflicted or of being susceptible to affliction with restenosis at some time subsequent to a surgical procedure to treat an atherosclerotic lesion. Further, while restenosis tends generally to occur at the same locus as a previous atherosclerotic lesion, it may not be exactly so, so a region of a segment of a vessel somewhat distant from the site of the initial atherosclerosis may in fact be the site of restenosis.

As used herein, a "vascular disease locale" refers to the location within a patient's body where an atherosclerotic lesion(s) is present, where restenosis may develop, the site of vulnerable plaque(s) or the site of a peripheral arterial disease.

An atherosclerotic lesion refers to a deposit of fatty substances, cholesterol, cellular waste products, calcium and/or fibrin on the inner lining or intima of an artery.

Restenosis refers to the re-narrowing or blockage of an artery at or near the site where angioplasty or another surgical procedure was previously performed to remove a stenosis.

Vulnerable plaque on the other hand is quite different from either atherosclerosis or restenosis and would generally come under the designation "suspected" affliction. This is because vulnerable plaque occurs primarily within the wall of a vessel and does not cause prominent protrusions into the lumen of the vessel. It is often not until it is "too late," i.e., until after a vulnerable plaque has broken and released its components into the vessel, that its presence is even known. Numerous methods have and are being investigated for the early diagnosis of vulnerable plaque but to date none have proven completely successful. Thus, the regional treatment of a segment of a vessel suspected of being afflicted with vulnerable plaque may be the best way to address such lesions.

As used herein, a peripheral arterial disease refers to a condition similar to coronary artery disease and carotid artery disease in which fatty deposits build up in the inner linings of the artery walls thereby restricting blood circulation, mainly in arteries leading to the kidneys, stomach, arms, legs and feet.

The present invention provides a novel bioactive agent-containing composition and a means of using such a composition for treating a range of vascular diseases. The composition will be delivered to a vascular disease locale by intraarterial delivery and in certain embodiments the microparticles and nanoparticles present in the composition can be delivered coaxially.

Once the composition is delivered to a disease locale, the size and shape disparity between the bioactive-containing nanoparticles and the microparticles provide a means for targeting the bioactive-containing nanoparticles to the vessel wall. Specifically, due to the non-spherical shape of the microparticles, they will tend to move with the flow of blood while more spherically-shaped bioactive agent-containing nanoparticles will be "pushed" to the side of the vessel, thereby accumulating at the vessel wall and the site of a vascular disease.

While not being bound to any particular theory, it is believed that the mechanism for this type of action is analogous to the flow of red blood cells, which are non-spherical, and the flow of more spherically shaped cell types, through the vasculature. Direct observations of red blood cell paths have shown that human ethryocytes migrate away from a vessel wall whereas more spherically shaped cells migrate towards the vessel wall. Several factors involved in this effect include the viscosity of the medium, i.e., the blood, the diameter of the blood vessel, the rotation of the cells, the size of the cells and the shape of the cells. However, of import to the present invention is the overall tendency for relatively small spherically-shaped cells to move towards the vessel wall while larger irregularly-shaped cells move away from the vessel wall, thereby moving more quickly through the vasculature.

The present invention builds on these observations by delivering bioactive agent-containing spherical or substantially spherical nanoparticles in conjunction with large non-spherical microparticles to the vasculature in order to treat a vascular disease.

In one embodiment, the composition may include nanoparticles and microparticles having the same or different bioactive agent(s). Indeed, the nanoparticles and microparticles may also possess different degradation rates and thus, different release rates. Methods of forming nanoparticles and microparticles, i.e., liposomes, with known degradation rates are known to those skilled in the art, as described in U.S. Pat. No. 6,451,338 to Gregoriadis et al., U.S. Pat. No. 6,168,804 to Samuel et al. and U.S. Pat. No. 6,258,378 to Schneider et al., which are hereby incorporated by reference in their entirety.

In certain embodiments, nanoparticles may possess triggered release capabilities, e.g., they may be thermo-, ultrasound- or light-sensitive. Thus, once nanoparticles are positioned at a vessel wall, they can be triggered to release a bioactive agent(s) by heating, light activation, or ultrasound. This may be done locally through a catheter-based intervention, e.g., heat or light, by an external device able to localize heat within a body, e.g., focused microwave radiation, or globally, e.g., by inducing fever or by ultrasound triggering, although in this latter case, the bioactive agent would still be localized by localization of the drug carrier. Methods of forming nanoparticles with triggered release capabilities are known to those skilled in the art.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A composition for delivering a bioactive agent, via intra-arterial injection, in a patient, comprising:
a plurality of substantially spherical or spherical polymeric nanoparticles and a plurality of non-spherical polymeric microparticles,
the nanoparticles comprising a first bioactive agent encapsulated within, adhered to a surface of or integrated into the structure of the nanoparticles, wherein the nanoparticles comprise a functional group operatively coupled to their surface with a binding affinity for a vessel wall in a patient, and wherein the first bioactive agent is released to a target locale in the patient; and
the microparticles having a high surface-area-to-volume ratio and optionally comprising a second bioactive agent that may be the same as, or different from, the first bioactive agent, encapsulated within, adhered to a surface of or integrated into the structure of the microparticles, wherein the size and shape disparity between the nanoparticles and the microparticles facilitates accumulation of the nanoparticles at the vessel wall;
wherein the smallest linear dimension of the microparticles is between about two and about four times larger than the largest linear dimension of the nanoparticles.

2. The composition according to claim 1, wherein the smallest linear dimension of the microparticles is at least three times larger than the largest linear dimension of the nanoparticles.

3. The composition according to claim 1, wherein the smallest linear dimension of the microparticles is at least two times larger than the largest linear dimension of the nanoparticles.

4. The composition according to claim 1, wherein the microparticles have a minimum linear dimension of 1.0 micron.

5. The composition according to claim 1, wherein the nanoparticles have a maximum linear dimension of 500 nanometers.

6. The composition according to claim 1, wherein the nanoparticles comprise a micelle, a liposome, a polymersome, a hydrogel particle or a polymer particle.

7. The composition according to claim 1, wherein the first and second bioactive agents are independently selected from the group consisting of corticosteroids, everolimus, zotarolimus, sirolimus, sirolimus derivatives, paclitaxel, -ApoA1, mutated ApoA1, ApoA1 milano, bisphosphonate, ApoA1 mimetic peptide, anti-inflammatory agents, anti-proliferative agents, anti-angiogenic agents, matrix metalloproteinase inhibitors, and tissue inhibitors of metalloproteinase.

8. The composition according to claim 1, wherein the microparticles are selected from the group consisting of a polymer particle, a polymersome and a hydrogel particle, wherein the hydrogel particle comprises a polymer selected from the group consisting of hyaluronic acid, poly(vinyl pyrrolidone), poly(ethylene glycol), albumin, poly(vinyl alcohol), gelatin, chitosan, alginate, fibrin and collagen.

9. The composition according to claim 1, wherein the microparticles are irregular-, oblong-, spindle-, rod-, cylindrical-, pancake-, discoid-, or red blood cell-shaped.

10. The composition according to claim 1, wherein the microparticles comprise a hydrogel particle.

11. The composition according to claim 10, wherein the hydrogel particle comprises a polymer selected from the group consisting of hyaluronic acid, poly(vinyl pyrrolidone), poly(ethylene glycol), albumin, poly(vinyl alcohol), gelatin, chitosan, alginate, fibrin and collagen.

12. The composition according to claim 1, wherein the nanoparticles and microparticles comprise the same polymer or polymers.

13. The composition according to claim 1, wherein the microparticles comprise carbon nanotubes.

14. The composition according to claim 13, wherein the carbon nanotubes are single or multi-walled.

15. The composition according to claim 1, wherein the microparticles comprise flexible polymeric cylinders.

16. The composition according to claim 1, wherein the microparticles comprise rigid polymeric cylinders.

17. The composition according to claim 1, wherein the microparticles comprise worm micelles.

18. The composition according to claim 1, wherein the microparticles comprise flexible polymeric or lipid membranes.

19. The composition according to claim 18, wherein the microparticles comprise a flaccid polymersome or flaccid liposome.

20. The composition according to claim 1, wherein the microparticles have a surface-area-to-volume aspect ratio between 0.1 and 100.

21. The composition according to claim 20, wherein the microparticles have a surface-area-to-volume aspect ratio between 1 and 10.

22. The composition according to claim 1, wherein the microparticles comprise a biodegradable or bioerodable material.

23. The composition according to claim 22, wherein the microparticles biodegrade or bioerode within 1.0 second to 100 hours.

24. The composition according to claim 23, wherein the microparticles biodegrade or bioerode within 10.0 seconds to 10 hours.

25. The composition according to claim 24, wherein the microparticles biodegrade or bioerode within 1.0 minute to 1 hour.

26. The composition according to claim 1, wherein the nanoparticles comprise a biodegradable or bioerodable material.

27. The composition according to claim 26, wherein the nanoparticles biodegrade or bioerode within 1.0 second to 100 hours.

28. The composition according to claim 27, wherein the nanoparticles biodegrade or bioerode within 10.0 seconds to 10 hours.

29. The composition according to claim 28, wherein the nanoparticles biodegrade or bioerode within 1.0 minute to 1 hour.

30. The composition according to claim 1, wherein the functional group comprises an intermediate component that couples the functional group to the surface of the nanoparticles.

31. The composition according to claim 1, wherein the functional group has binding affinity for endothelium.

32. The composition according to claim 31, wherein the functional group is a peptide, a protein or an oligonucleotide.

33. The composition according to claim 31, wherein the functional group has a charge.

34. A method for treating a vascular disease comprising: administering the composition according to claim 1 to a vascular disease locale in a patient.

35. The method according to claim 34, wherein administering the composition to the vascular disease locale in the patient comprises intraarterial delivery.

36. The method according to claim 35, wherein intraarterial delivery comprises percutaneous transluminal coronary arterial delivery.

37. The method according to claim 35, wherein intraarterial delivery comprises coaxial delivery of the nanoparticles and microparticles.

38. The method according to claim 35, wherein intraarterial delivery comprises using a catheter.

39. The method according to claim 38, wherein the catheter comprises a guiding, diagnostic or drug delivery catheter.

40. A composition for delivering a bioactive agent, via intra-arterial injection, in a patient, comprising:
   a plurality of substantially spherical or spherical polymeric nanoparticles and a plurality of non-spherical polymeric microparticles,
      the nanoparticles comprising a first bioactive agent encapsulated within, adhered to a surface of or integrated into the structure of the nanoparticles, wherein the nanoparticles comprise a functional group operatively coupled to their surface with a binding affinity for a vessel wall in a patient, and wherein the first bioactive agent is released to a target locale in the patient; and
   the microparticles optionally comprising a second bioactive agent that may be the same as, or different from, the first bioactive agent, encapsulated within, adhered to a surface of or integrated into the structure of the microparticles, wherein the size and shape disparity between the nanoparticles and the microparticles facilitates accumulation of the nanoparticles at the vessel wall;
   wherein the smallest linear dimension of the microparticles is between about two and about four times larger than the largest linear dimension of the nanoparticles, and the microparticles have a surface-area-to-volume aspect ratio between 0.1 and 100.

41. The composition according to claim 40, wherein the microparticles have a surface-area-to-volume aspect ratio between 1 and 10.

\* \* \* \* \*